(12) United States Patent
Wisniewski

(10) Patent No.: US 11,517,738 B2
(45) Date of Patent: Dec. 6, 2022

(54) INLET CANNULA FOR A FLUID PUMP

(71) Applicant: Berlin Heart GmbH, Berlin (DE)

(72) Inventor: Adrian Wisniewski, Berlin (DE)

(73) Assignee: Berlin Heart GmbH, Berlin (DE)

( * ) Notice: Subject to any disclaimer, the term of this patent is extended or adjusted under 35 U.S.C. 154(b) by 250 days.

(21) Appl. No.: 16/764,545

(22) PCT Filed: Nov. 15, 2018

(86) PCT No.: PCT/EP2018/081462
§ 371 (c)(1),
(2) Date: May 15, 2020

(87) PCT Pub. No.: WO2019/096948
PCT Pub. Date: May 23, 2019

(65) Prior Publication Data
US 2021/0170164 A1 Jun. 10, 2021

(30) Foreign Application Priority Data
Nov. 16, 2017 (EP) .................................... 17202085

(51) Int. Cl.
*A61M 60/178* (2021.01)
*A61M 60/857* (2021.01)
*A61M 60/861* (2021.01)

(52) U.S. Cl.
CPC ........ *A61M 60/178* (2021.01); *A61M 60/857* (2021.01); *A61M 60/861* (2021.01); *A61M 2205/04* (2013.01)

(58) Field of Classification Search
CPC .............. A61M 60/857; A61M 60/178; A61M 60/122; A61M 60/148; A61M 2205/04
See application file for complete search history.

(56) References Cited

U.S. PATENT DOCUMENTS

| 6,050,975 A | * | 4/2000 | Poirier | ............... | A61M 60/422 |
| | | | | | 604/151 |
| 8,894,561 B2 | * | 11/2014 | Callaway | .............. | A61M 60/50 |
| | | | | | 600/16 |
| 2007/0299297 A1 | | 12/2007 | Jarvik | | |

(Continued)

OTHER PUBLICATIONS

International Search Report with English translation, issued in International Application No. PCT/EP2018/081462, pp. 1-6, European Patent Office, Rijswijk, Netherlands.

*Primary Examiner* — Paula J Stice
(74) *Attorney, Agent, or Firm* — Crowell & Moring LLP

(57) ABSTRACT

An inlet cannula is provided for supplying a fluid from a human vessel to a fluid pump, the inlet cannula formed as a hollow structure suitable for conveying the fluid and a surface of the inlet cannula has an ingrowth zone and an inlet zone separated from each other by a tear-off edge extending in the circumferential direction of the inlet cannula, wherein a first tangent to the inlet zone on the tear-off edge has an angle to a longitudinal axis of the inlet cannula of >0° and <180°, and wherein a surface roughness in the ingrowth zone is greater than a surface roughness in the inlet zone, and wherein along the flow direction the ingrowth zone is concave, convex, or not curved and the inlet zone is convexly curved, and wherein the tear-off edge forms a curvature transition between the ingrowth zone and the inlet zone.

17 Claims, 4 Drawing Sheets

(56) References Cited

U.S. PATENT DOCUMENTS

2012/0059213 A1 3/2012 Spence
2012/0095281 A1 4/2012 Reichenbach et al.
2012/0143141 A1 6/2012 Verkaik et al.
2014/0257018 A1 9/2014 Farnan \* cited by examiner

INLET CANNULA FOR A FLUID PUMP

CROSS-REFERENCE TO RELATED APPLICATIONS

This application is a 371 nationalization of international patent application PCT/EP2018/081462 filed Nov. 15, 2018, which claims priority under 35 USC § 119 to European patent application 17202085.1 filed Nov. 16, 2017. The entire contents of each of the above-identified applications are hereby incorporated by reference.

TECHNICAL FIELD

The present invention relates to an inlet cannula for supplying a fluid from a human vessel, and to a fluid pump system comprising an inlet cannula and a fluid pump.

BACKGROUND

In the prior art, inlet cannulas for heart pumps are known, which guide blood from a ventricle into a blood pump. Along the outer surfaces, the inlet cannulas, in general, include a structured region having increased surface roughness. The structuring is intended to allow the inlet cannula to grow into the ventricle wall. Inlet cannulas are generally polished in the region of the inlet opening, so that the surface roughness is minimal there. This, in turn, is to allow for a uniform and uninhibited flow of blood into the inlet cannula. Nonetheless, the inlet cannulas known from the prior art have a design that carries a high risk of thrombus formation due to disturbance of the blood flow at the inlet of the inlet cannula. The known inlet cannulas furthermore carry the risk of thrombi from the ventricle reaching the inlet cannula, and then also the blood pump, and clogging it.

DETAILED DESCRIPTION

Figure 1:
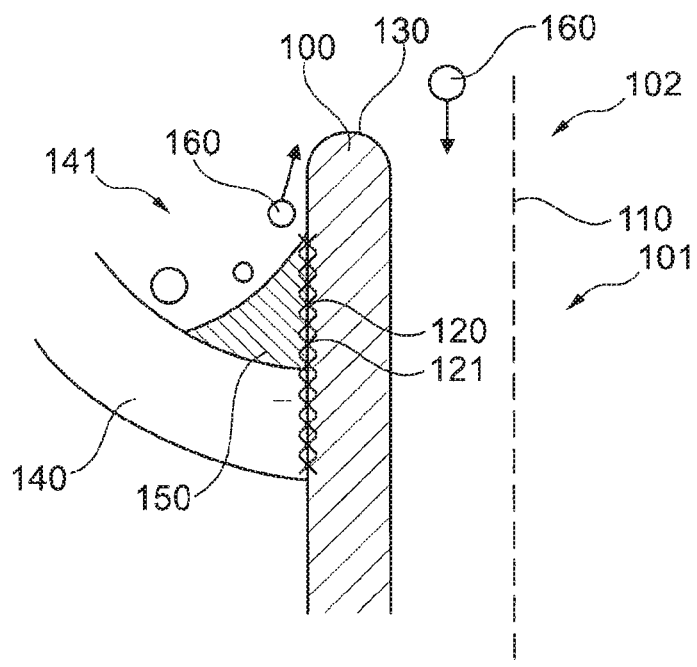
FIG. 1 shows a schematic representation of an ingrowth behavior and flood flow in an inlet cannula from the prior art.

It is therefore an object of the present invention to provide an inlet cannula for a fluid pump which allows fluid to flow undisturbed and evenly into the fluid pump, and minimizes the risk of thrombi forming and being introduced into the fluid pump. It is a further object of the present invention to provide a fluid pump system comprising such an inlet cannula and a fluid pump.

An inlet cannula according to the invention for supplying a fluid, in particular blood, from a human vessel into a fluid pump is designed as a hollow structure suitable for guiding the fluid. A surface of the inlet cannula comprises an ingrowth zone and an inlet zone, successively in a flow direction of the fluid.

The surface of the inlet cannula shall be understood to mean the entire surface of the inlet cannula designed as a hollow structure, that is, both the outer surface facing the human vessel and the inner surface facing an interior of the inlet cannula. Moreover, a flow direction of the fluid shall be understood to mean a flow direction of at least a fluid portion from the human vessel into the inlet cannula, and in particular also from a region of the human vessel located around the outer surface of the inlet cannula.

In the inlet cannula according to the invention, the ingrowth zone and the inlet zone are separated from one another by a flow separation edge extending in the circumferential direction of the inlet cannula, wherein a first tangent to the inlet zone at the flow separation edge has an angle with respect to a longitudinal axis (hereafter also alternatively referred to as a center line) of the inlet cannula of >0° and <180°.

The flow separation edge shall be understood to mean a clear, geometric edge along the circumference of the inlet cannula, which protrudes from the otherwise smooth (apart from surface roughness) outer surface of the inlet cannula. The flow separation edge separates the ingrowth zone and the inlet zone from one another and, per se, does not form part of either the ingrowth zone or the inlet zone. This clear, geometric edge and a region of the inlet zone directly adjoining the flow separation edge can be superimposed by surface irregularities due to material-specific and/or manufacturing-related surface roughness. The mean roughness depth of these surface irregularities, however, is small compared to a mean height of the flow separation edge, which can be determined, for example, with respect to an interval around the flow separation edge, having a length that corresponds to an average thickness of a wall of the inlet cannula. For manufacturing-related reasons, the flow separation edge can have a maximum radius of up to 0.5 mm.

A first tangent to the inlet zone at the flow separation edge shall be understood to mean a tangent in a region of the inlet zone that directly adjoins the flow separation edge. Furthermore, a first tangent to the flow separation edge shall be understood to mean only a tangent to the clear, geometric flow separation edge, and not to an edge based on surface irregularity.

Moreover, a surface roughness in the ingrowth zone of the inlet cannula according to the invention is greater than a surface roughness in the inlet zone.

The ingrowth zone has either a concave, a convex or no curvature, and the inlet zone has a convex curvature, wherein the inlet zone is convexly curved with a radius of curvature of 2 to 20 mm, or the ingrowth zone is convexly curved, and the inlet zone is not curved. The flow separation edge forms a transition in the curvature between the ingrowth zone and the inlet zone.

The following combinations of curvatures of the ingrowth zone and the inlet zone are particularly preferred: The ingrowth zone is not curved, wherein the ingrowth zone extends parallel to the longitudinal axis of the inlet cannula, and the inlet zone is convex. The ingrowth zone is concave, and the inlet zone is convex. The ingrowth zone and the inlet zone are convex. The ingrowth zone is convex, and the inlet zone is not curved, wherein the inlet zone extends at an angle, which opens toward the inlet opening, with respect to the longitudinal axis of the inlet cannula.

The flow separation edge of the inlet cannula according to the invention thus represents a clear, geometric separation between the ingrowth zone and the inlet zone which is not just defined by the surface roughness. Due to the flow separation edge, the wall shear stress in the inlet zone in the region of an inlet opening of the inlet cannula is increased, so that a lower risk exists of thrombi forming at the inlet opening, and of thrombi being introduced into the inlet cannula.

In particular, the first tangent can have an angle with respect to the longitudinal axis of the inlet cannula between 10° and 170°, preferably between 30° and 160°, particularly preferably between 85° and 95°, in particular of 90°, or between 60° and 70°, or between 110° and 130°, or between 145° and 155°. The inlet cannula can have a rotation-symmetrical design. In this case, the longitudinal axis corresponds to the axis of symmetry of the rotational symmetry.

In an advantageous embodiment of the inlet cannula according to the invention, the inlet zone, at least along a distance of up to half the average thickness of a wall of the inlet cannula from the flow separation edge, can extend at an angle of >0° and <180°, in particular between 10° and 170°, preferably between 30° and 160°, particularly preferably between 85° and 95°, in particular of 90°, or between 60° and 70°, or between 110° and 130°, or between 145° and 155°.

In a further embodiment of the inlet cannula according to the invention, the flow separation edge extends continuously in the circumferential direction of the inlet cannula. This has the advantage that a preferably undisturbed fluid flow is ensured around the entire inlet cannula, and that high wall shear stress is ensured between the fluid and the inlet zone.

The inlet cannula according to the invention preferably comprises or consists of a hemocompatible material, in particular titanium, a titanium alloy, in particular $Ti_6Al_4V$, stainless steel and/or plastic.

In a further advantageous embodiment of the invention, the ingrowth zone includes a texturing. The texturing can only be present in a portion of the ingrowth zone or can completely cover the ingrowth zone. The texturing can take place by way of a sintering process, a 3D printing process, in particular for imprinting a titanium texturing, by way of bombardment with small spheres, in particular small titanium spheres, and/or by way of adhesive bonding of a continuous fabric, in particular velours. The texturing can have a mean roughness depth of Rz>16 μm.

It is furthermore advantageous when the inlet zone is polished, wherein the polished inlet zone can, in particular, have a mean roughness depth of Rz<1.5 μm.

The ingrowth zone can be concavely or convexly curved with a radius of curvature of 2 to 20 mm, preferably 5, 10 or 15 mm.

The inlet zone can be convexly curved with a radius of curvature of preferably 5, 10 or 15 mm.

It is furthermore advantageous when the first tangent to the inlet zone and a second tangent to the ingrowth zone at the flow separation edge intersect at an angle between 40° and 150°, and in particular at an angle of 90°.

In an advantageous embodiment of the present invention, wall shear stress of 1 to 10 Pa, in particular of 2 Pa, preferably of 4 Pa, can be present between the fluid and inlet zone, at a mean volume flow of the fluid of 2 to 10 L/min, and in particular 4.5 L/min, and/or wall shear stress of <1 Pa can be present in the ingrowth zone. It is particularly advantageous when a jump in wall shear stress between the fluid and the surface of the inlet cannula of at least 100% results at the transition from the ingrowth zone to the inlet zone, preferably in a region having a distance from the flow separation edge of up to 1 mm. Directly around the flow separation edge, a fluid flow can also detach slightly from the surface of the inlet cannula, resulting in a decrease in the wall shear stress directly at the edge.

In particular, at a mean volume flow of the fluid of 4.5 L/min, wall shear stress of >1 Pa can be present in the ingrowth zone with respect to a flow direction of the fluid at a distance from the flow separation edge of no more than 0.75 mm, wall shear stress of <0.25 Pa can be present at a distance from the flow separation edge of no more than 0.8 mm, wall shear stress of <0.5 Pa can be present at a distance from the flow separation edge of no more than 0.4 mm, and wall shear stress of <0.75 Pa can be present at a distance from the flow separation edge of no more than 0.2 mm. In the inlet zone, with respect to a flow direction of the fluid, wall shear stress of >0.75 Pa can be present directly downstream from the flow separation edge, wall shear stress of >1 Pa can be present at a distance from the flow separation edge of no more than 0.75 mm, wall shear stress of >2 Pa can be present at a distance from the flow separation edge of no more than 1.5 mm, and wall shear stress of >4 Pa can be present at a distance from the flow separation edge of no more than 2.5 mm.

At a distance of ≤5 mm from the flow separation edge, the surface roughness in the ingrowth zone can furthermore be identical to the surface roughness in the inlet zone. This is the case, for example, when the texturing, for process-related reasons, cannot be applied directly up to the flow separation edge in the ingrowth zone.

So as to connect the inlet cannula to a fluid pump, the inlet cannula can furthermore comprise a pump interface, wherein the pump interface can be positioned outside the human vessel, and a pump inlet of the fluid pump can be connected to the pump interface.

It is furthermore advantageous when a third tangent perpendicular to the flow separation edge at the inlet zone, in a region of the inlet zone adjacent to the pump interface, has an angle between 0° and 30°, in particular of 10°, 15° or 20° with respect to a longitudinal axis of the inlet cannula.

In a further advantageous embodiment of the invention, the inlet opening of the inlet cannula is arranged in a region of the inlet zone adjacent to the flow separation edge, wherein a lattice element, which partially closes the inlet opening, is arranged in the inlet opening. The lattice element can comprise a center part and two, three or four arms connected to the center part, wherein the center part extends along the longitudinal axis in the center of the inlet cannula, and the arms extend along the inlet zone into the inlet cannula. The lattice element can be used to prevent or minimize a suction effect of the cardiac wall at the inlet cannula. Furthermore, it would be conceivable for the lattice element to prevent solidified fluid particles (such as thrombi, if the fluid is blood, trabeculae, clots, ingrowth structures or muscle tissue) from penetrating into the inlet cannula.

The inlet cannula can, in particular, cooperate with a fluid pump, which comprises a non-rotating, inlet-side, radially centrally arranged bearing element. The inlet-side bearing can absorb radial and axial forces and moments. The lattice element can be designed such that the center part forms a hub, which extends along the longitudinal axis through the inlet cannula and holds a stationary part of the bearing of the fluid pump.

The invention furthermore comprises a fluid pump system, comprising an above-described inlet cannula and a fluid pump, wherein the pump interface of the inlet cannula is connected to the pump inlet of the fluid pump.

An inlet cannula according to the invention, and a fluid pump system according to the invention, are described hereafter in greater detail based on figures. Different elements that are essential to the invention, or elements providing advantageous refinements, are described in each case within the scope of a specific example, wherein it is also possible to use individual of these elements per se to refine the invention, including detached from the context of the particular example and further features of the particular example. Moreover, identical or similar reference numerals are used for identical or similar elements in the figures, and the explanation thereof is therefore partially omitted.

Figure 2:
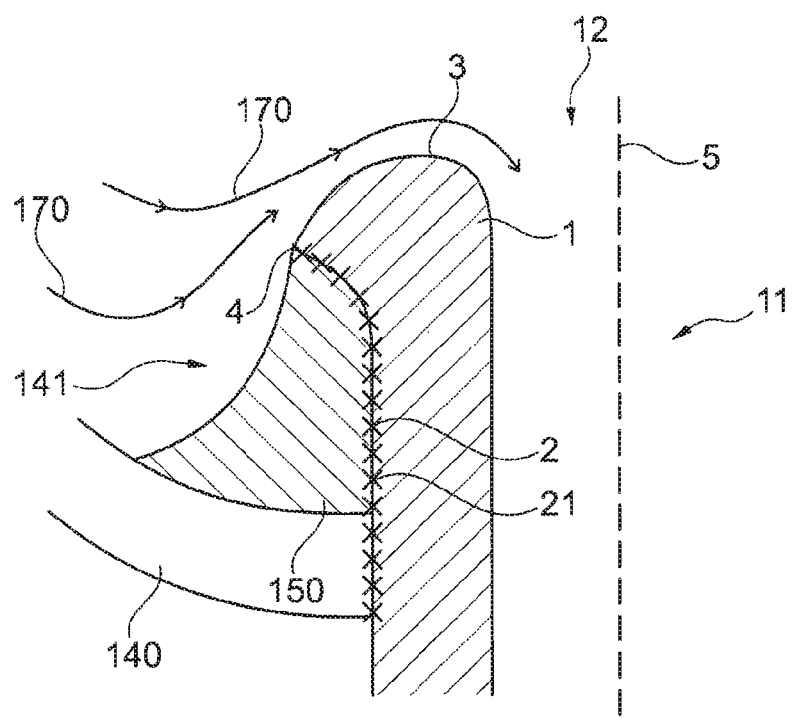
FIG. 2 shows a schematic representation of an ingrowth behavior and flood flow in an inlet cannula according to the invention.
Figure 5:
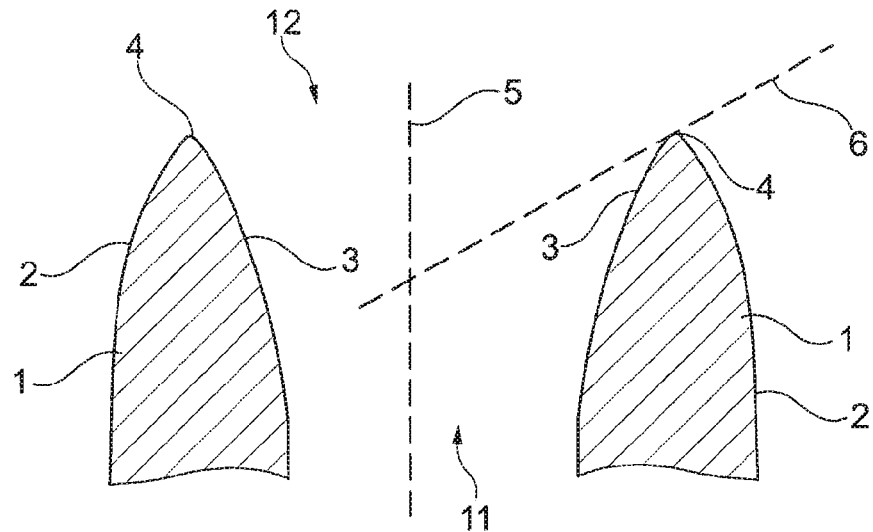
FIG. 5 shows schematic sectional view of an inlet cannula according to the invention having a third geometry.
Figure 6:
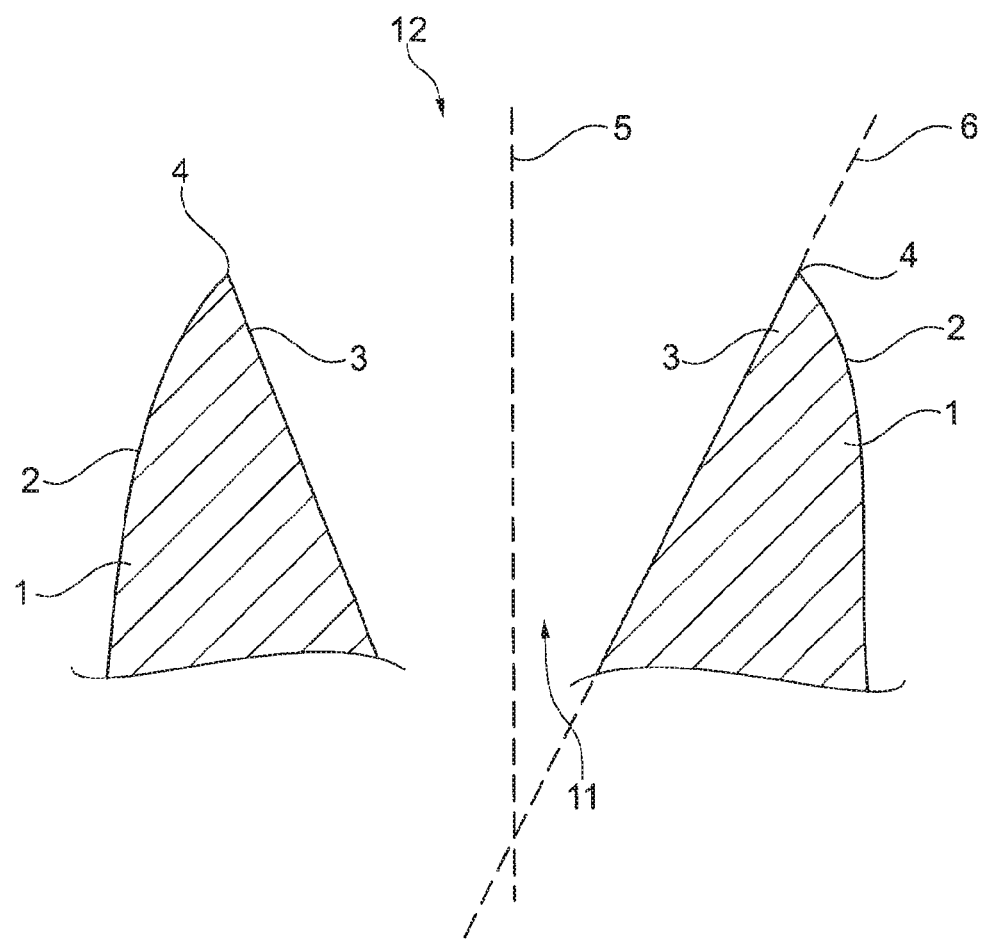
FIG. 6 shows schematic sectional view of an inlet cannula according to the invention having a fourth geometry.
Figure 7:
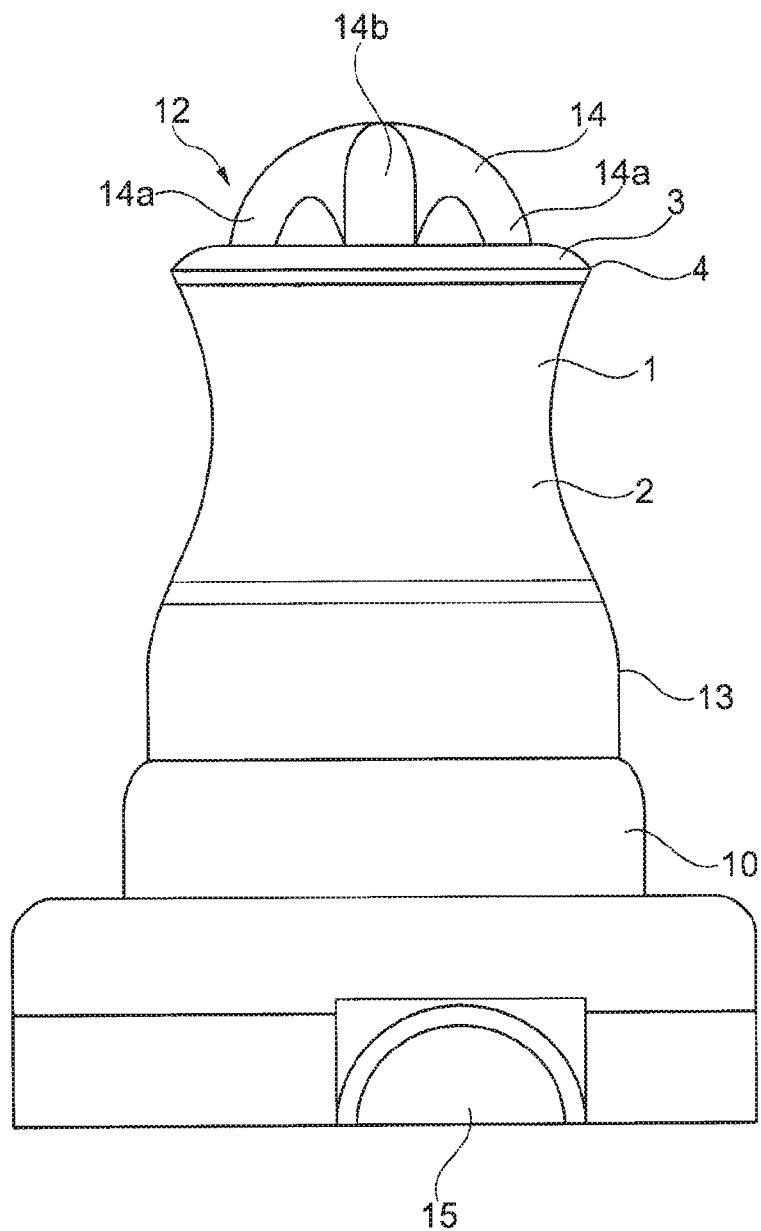
FIG. 7 shows a schematic representation of a fluid pump system according to the invention.

In the drawings:

FIG. 1 shows a schematic representation of an ingrowth behavior and flood flow in an inlet cannula from the prior art;

FIG. 2 shows a schematic representation of an ingrowth behavior and flood flow in an inlet cannula according to the invention;

FIGS. 3 to 6 show schematic sectional views of inlet cannulas according to the invention having different geometries; and FIG. 7 shows a schematic representation of a fluid pump system according to the invention.

THE FOLLOWING REFERENCE NUMERALS ARE USED IN THE FIGURES 1, 100 inlet cannula
11, 101 inner cavity
2, 120 ingrowth zone
21, 121 texturing
3, 130 inlet zone
4 flow separation edge
5, 110 longitudinal axis
6 first tangent
10 fluid pump
12 inlet opening
13 pump housing
14 lattice element
14a center part
14b arms
15 fluid outlet
140 ventricle wall
141 ventricle
150 adhering tissue
160 thrombi/tissue/particles
170 blood flow The exemplary embodiments described hereafter primarily relate to inlet cannulas for supplying blood from a ventricle into a blood pump. FIG. 1 shows an inlet cannula 100 according to the prior art, which is introduced through an opening in a ventricle wall 140 into a ventricle 141, in a sectional view parallel to a longitudinal axis 110 of the inlet cannula 100. The inlet cannula 100 has a hollow cylindrical design. FIG. 1 only shows a portion of the inlet cannula 100. The inlet cannula 100 includes an inner cavity 101 and is rotation-symmetrical with respect to the longitudinal axis 110. On an outer surface located toward the ventricle wall 140 and toward the ventricle 141, the inlet cannula 100 comprises an ingrowth zone 120, which is provided with a texturing 121. Along the ingrowth zone 120, ingrowth of the inlet cannula 100 is desirable, which is why the texturing 121 is applied in this region so as to increase the surface roughness. In the region of an inlet opening 102 of the inlet cannula 100, an inlet zone 130 extends from the outer surface via the inlet opening 102 to an inner surface facing the inner cavity 101. In contrast to the ingrowth zone 120, the inlet zone 130 is not textured. Rather, the inlet zone 130 is polished so as to minimize the surface roughness in order to obtain unobstructed blood flow in this region. On the outer surface, the ingrowth zone 120 and the inlet zone 130 transition smoothly into one another in the direction of the flow of a portion of the blood. A boundary between the ingrowth zone 120 and the inlet zone 130 is only apparent based on the changing surface finish (textured/polished).

It is apparent in FIG. 1 that tissue 150 has formed along the textured ingrowth zone 120, which connects the inlet cannula 100 to the ventricle wall 141, so that the inlet cannula 100 can no longer slide out of the ventricle 140. However, the blood flow in the direction of the inlet zone 130 of the inlet cannula 100 is disturbed in the region of the adhering tissue 150, which brings with it a high risk of the formation of thrombi 160. These thrombi 160 can then reach the inlet zone 130 and the interior 101 of the inlet cannula 100. From there, these thrombi 160 can reach a connected blood pump (not shown in FIG. 1) and clog or block it. It is also possible for adhering tissue 150, which grows beyond the ingrowth zone, to extend from the ingrowth zone 2 further into the inlet zone 3 and, from there, reach the interior of the inlet cannula 100, and to clog or block the connected blood pump.

FIG. 2 shows a situation similar to that of FIG. 1, using an inlet cannula 1 according to the invention. The inlet cannula 1 according to the invention has a hollow cylindrical design and includes an inlet opening 12 and an inner cavity 11. In contrast to the inlet cannula 100 known from the prior art, the inlet opening 12 of the inlet cannula 11 is flared in a trumpet-shaped manner at the outer surface. The outer surface of the inlet cannula 1 located toward the interior of the ventricle 141 and toward the ventricle wall 140 likewise comprises an ingrowth zone 2 and an inlet zone 3 in the flow direction of at least a portion of the blood, wherein the inlet zone 3 extends from the outer surface of the inlet cannula 1 via the inlet opening 12 to the inner surface located toward the inner cavity 11. In contrast to the inlet cannula 100 from the prior art, the ingrowth zone 2 and the inlet zone 3 are clearly separated from one another by a flow separation edge 4 extending in the circumferential direction of the inlet cannula 1. So as to promote ingrowth, the ingrowth zone 2 includes a texturing 21 and is concavely curved. The inlet zone 3 is polished so as to improve blood flow, and has a convex curvature. The flow separation edge 4 thus represents a sudden transition in curvature between the concave curvature of the ingrowth zone 2 and the convex curvature of the inlet zone 3.

It is apparent in FIG. 2 that, similarly to FIG. 1, tissue 150 has formed along the ingrowth zone 2, whereby the inlet cannula 1 can no longer slide out of the ventricle 141. The tissue 150 adheres cleanly up to the flow separation edge 4 and thus forms an advantageous connection, in terms of flow, between the inner surface of the ventricle wall 140 facing the interior of the ventricle 141 and the inlet zone 3. This results in considerably higher wall shear stress between the blood and the inlet zone 3 in the region of the inlet opening 12, and in undisturbed blood flow 170 from an edge region of the ventricle 141 adjacent to the ingrowth zone 2 into the inlet cannula 1. In the inlet cannula 1 according to the invention, the flow separation edge 4 thus prevents ingrowth of the inlet cannula beyond the ingrowth zone 3, and consequently a risk of tissue 150 reaching the inlet cannula 1. Moreover, thrombi and other particles (trabeculae, tissue particles) are retained in the edge region of the ventricle 141 by the flow separation edge 4 and do not reach the inlet cannula 1. The risk of the formation of thrombi can also be decreased compared to the inlet cannula 100 from the prior art.

Figure 3:
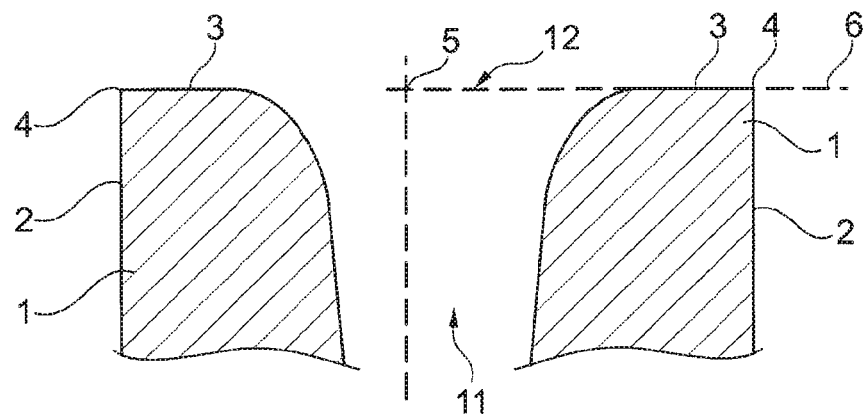
FIG. 3 shows schematic sectional view of an inlet cannula according to the invention having a first geometry.

FIG. 3 shows a further exemplary embodiment of an inlet cannula 1 according to the invention in a schematic sectional view parallel to the longitudinal axis 5. The inlet cannula 1 is designed as an open hollow structure having a cylindrical outer surface. Along the outer surface, the inlet cannula 1 comprises a non-curved ingrowth zone 2. In the region of the inlet opening 12, the ingrowth zone 2 is delimited by a flow separation edge 4 extending in the circumferential direction. An inlet zone 3 extends from the flow separation edge 4 to an inner surface facing an inner cavity 11 of the inlet cannula 1. The inlet zone 3 is convexly curved so that an inside diameter of the inlet cannula decreases, leading away from the inlet opening 12. The flow separation edge 4 is furthermore designed so that a tangent 6 to the inlet zone 3 at the flow separation edge 4 extends at an angle of approximately 90° with respect to the longitudinal axis 5.

Figure 4:
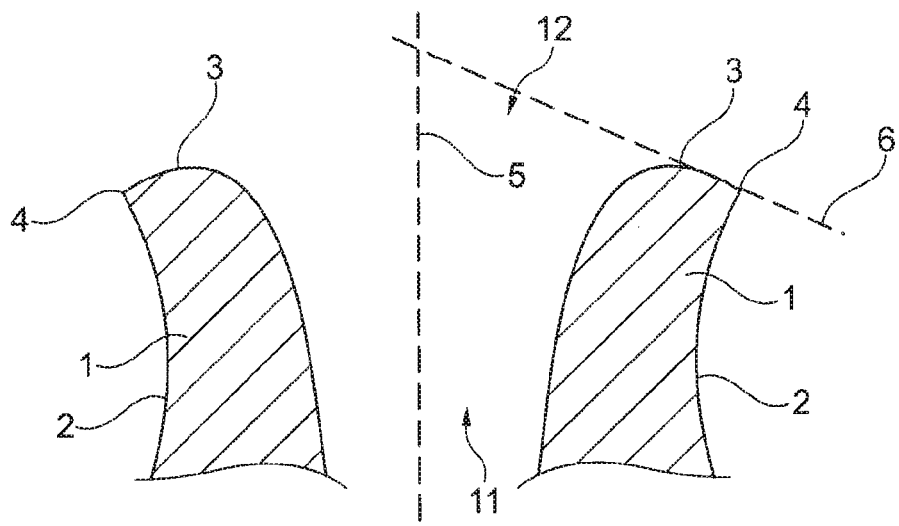
FIG. 4 shows schematic sectional view of an inlet cannula according to the invention having a second geometry.

FIG. 4 shows a further exemplary embodiment of an inlet cannula 1 according to the invention in a representation similar to that of FIG. 3. In contrast to the inlet cannula 1 of FIG. 3, the ingrowth zone 2 of the inlet cannula 1 in FIG. 4 has a concave curvature, whereas the inlet zone 3 is likewise convexly curved. The flow separation edge 4 thus represents a sudden transition in curvature between the concave curvature in the ingrowth zone 2 and the convex curvature in the inlet zone 3. The flow separation edge 4 is furthermore designed so that a tangent 6 to the inlet zone at the flow separation edge extends at an angle of approximately 65°, which is open toward the inner cavity 11, with respect to the longitudinal axis 5. Furthermore, the inside diameter of the inlet cannula 1 tapers with increasing distance from the inlet opening 12.

FIG. 5 shows a further exemplary embodiment of an inlet cannula 1 according to the invention in a representation similar to that of FIGS. 3 and 4. In contrast to the inlet cannula 1 of FIGS. 3 and 4, the ingrowth zone 2 and the inlet zone 3 of the inlet cannula 1 in FIG. 5 have a convex curvature. The flow separation edge 4 thus represents a sudden transition in curvature between the two convex curvatures. Moreover, the flow separation edge 4 is shifted toward the center line 5 of the inlet cannula 1, so that a diameter of the inlet cannula 1 at the level of the flow separation edge 4 is between a maximum outside diameter and an inside diameter of the inlet cannula 1. The flow separation edge 4 is furthermore designed so that a tangent 6 to the inlet zone 3 at the flow separation edge 4 extends at an angle of approximately 120°, which is open toward the inner cavity 11, with respect to the longitudinal axis 5. Furthermore, the inside diameter of the inlet cannula 1 tapers with increasing distance from the inlet opening 12.

FIG. 6 shows a further exemplary embodiment of an inlet cannula 1 according to the invention in a representation similar to that of FIGS. 3 to 5. The ingrowth zone 2 of the inlet cannula 1 in FIG. 5 has a convex curvature, whereas the inlet zone 3 is not curved. The flow separation edge 4 thus represents a transition in curvature between the convex curvature in the ingrowth zone 2 and the non-existent curvature in the inlet zone 3. The flow separation edge 4 is furthermore designed so that a tangent 6 to the inlet zone 3 at the flow separation edge 4 extends at an angle of approximately 155°, which is open toward the inner cavity 11, with respect to the longitudinal axis 5. The inlet zone 3 extends at an acute angle, which is open toward the inlet opening 12, with respect to the longitudinal axis 5. As a result, the inside diameter of the inlet cannula 1 tapers with increasing distance from the inlet opening 12. Similarly to FIG. 5, the flow separation edge 4 of the inlet cannula 1 in FIG. 6 is shifted toward the center line 5 of the inlet cannula 1, so that a diameter of the inlet cannula 1 at the level of the flow separation edge 4 is between a maximum outside diameter and an inside diameter of the inlet cannula 1.

FIG. 7 shows a schematic representation of a fluid pump system according to the invention, comprising an inlet cannula 1 and a fluid pump 10. The inlet cannula 1 comprises an ingrowth zone 2 and an inlet zone 3, which are separated from one another in the region of the inlet opening 12 by a flow separation edge 4. A lattice element 14 is arranged in the inlet opening 12, which protrudes from the inlet cannula 1 and partially closes the inlet opening 12. The lattice element 14 comprises two opposing arms 14a and a center part 14b, which connects the arms 14a to one another. The arms 14a extend in an arcuate manner from the center part 14b to the inner surface of the inlet cannula 1. The center part 14b furthermore forms a hub (not shown here), which extends along the center line 5 (longitudinal axis) of the inlet cannula 1 into the inner cavity 11 of the inlet cannula 1. The center part 14b designed as a hub holds a stationary part of the bearing of the fluid pump 10 in the interior cavity 11. The arms 14a extend in the direction of the longitudinal axis 5 along the inner surface of the inlet cannula 1 and are supported on the inner surface. The lattice element 14 is furthermore used to prevent or minimize a suction effect of the cardiac wall against the inlet opening. It is furthermore conceivable for the lattice element to additionally prevent thrombi, which may be present in the region of the inlet cannula, from flowing in. A pump housing 13 of the fluid pump 10 is connected on a side of the inlet cannula 1 facing away from the inlet opening 12. The fluid pump 10 is, in particular, a pump that delivers the fluid in the direction of the longitudinal axis 5 from the inlet opening 12 to a fluid outlet 15.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The present invention furthermore includes the following aspects:

1. An inlet cannula for supplying a fluid from a human vessel into a fluid pump, wherein the inlet cannula is designed as a hollow structure suitable for guiding the fluid, and
 a surface of the inlet cannula comprises an inlet zone and an ingrowth zone, successively in a flow direction of the fluid,
 wherein the ingrowth zone and the inlet zone are separated from one another by a flow separation edge extending in the circumferential direction of the inlet cannula, wherein a first tangent to the inlet zone at the flow separation edge has an angle with respect to a longitudinal axis of the inlet cannula of >0° and <180°, and wherein a surface roughness in the ingrowth zone is greater than a surface roughness in the inlet zone.
2. The inlet cannula according to the preceding aspect, characterized in that the first tangent has an angle with respect to the longitudinal axis of the inlet cannula between 10° and 170°, preferably between 30° and 160°, particularly preferably between 85° and 95°, in particular of 90°, or between 60° and 70°, or between 110° and 130°, or between 145° and 155°.
3. The inlet cannula according to any one of the preceding aspects, characterized in that the flow separation edge extends continuously in the circumferential direction of the inlet cannula.
4. The inlet cannula according to any one of the preceding aspects, characterized in that the ingrowth zone includes a texturing, and in particular that the ingrowth zone includes a texturing in a portion or throughout.
5. The inlet cannula according to the preceding aspect, characterized in that the texturing can take place by way of a sintering process, a 3D printing process, in particular for imprinting a titanium texturing, by way of bombardment with small spheres, in particular small titanium spheres, and/or by way of adhesive bonding of a continuous fabric, in particular velours.
6. The inlet cannula according to any one of the two preceding aspects, characterized in that the texturing has a mean roughness depth of Rz>16 μm.
7. The inlet cannula according to any one of the preceding aspects, characterized in that the inlet zone is polished, the polished inlet zone having, in particular, a mean roughness depth of Rz<1.5 μm.
8. The inlet cannula according to any one of the preceding aspects, characterized in that the ingrowth zone has a concave, a convex or no curvature along the flow direction, and the inlet zone has a convex or no curvature, the flow separation edge forming a transition in the curvature between the ingrowth zone and the inlet zone.
9. The inlet cannula according to the preceding aspect, characterized in that the ingrowth zone is concavely or convexly curved with a radius of curvature of 2 to 20 mm, and preferably 5, 10 or 15 mm.
10. The inlet cannula according to any one of the two preceding aspects, characterized in that the inlet zone is convexly curved with a radius of curvature of 2 to 20 mm, and preferably 5, 10 or 15 mm.
11. The inlet cannula according to any one of the three preceding aspects, characterized in that the first tangent to the inlet zone and a second tangent to the ingrowth zone at the flow separation edge intersect at an angle between 40° and 150°, and in particular at an angle of 90°.
12. The inlet cannula according to any one of the preceding aspects, characterized in that a jump in wall shear stress between the fluid and the surface of the inlet cannula of at least 100% results at the transition from the ingrowth zone to the inlet zone.
13. The inlet cannula according to the preceding aspect, characterized in that the inlet cannula includes a pump interface for connecting the inlet cannula to a fluid pump, and a third tangent perpendicularly to the flow separation edge to the inlet zone in a region of the inlet zone adjacent to the pump interface has an angle between 0° and 30° with respect to a longitudinal axis of the inlet cannula.
14. The inlet cannula according to any one of the preceding aspects, characterized in that the inlet cannula has an inlet opening in a region of the inlet zone adjacent to the flow separation edge, and a lattice element, which partially closes the inlet opening, is arranged in the inlet opening.
15. A fluid pump system, comprising an inlet cannula according to any one of the preceding aspects and a fluid pump, the pump interface of the inlet cannula being connected to the pump inlet of the fluid pump.

The invention claimed is:
1. An inlet cannula for supplying a fluid from a human vessel into a fluid pump, wherein the inlet cannula is a hollow structure suitable for guiding the fluid, and
  a surface of the inlet cannula comprises an ingrowth zone and an inlet zone, successively in a flow direction of the fluid,
  the ingrowth zone and the inlet zone being separated from one another by a flow separation edge extending in the circumferential direction of the inlet cannula, a first tangent to the inlet zone at the flow separation edge having an angle with respect to a longitudinal axis of the inlet cannula of >0° and <180°, and
  a surface roughness in the ingrowth zone being greater than a surface roughness in the inlet zone, and
  the ingrowth zone having a concave, a convex, or no curvature along the flow direction, and the inlet zone having a convex curvature, the inlet zone being convexly curved with a radius of curvature of 2 to 20 mm, or
  the ingrowth zone being convexly curved, and the inlet zone not being curved,
  and the flow separation edge forming a transition in the curvature between the ingrowth zone and the inlet zone.
2. The inlet cannula of claim 1, wherein the first tangent has an angle with respect to the longitudinal axis of the inlet cannula between 10° and 170°.
3. The inlet cannula of claim 1, wherein the flow separation edge extends continuously in the circumferential direction of the inlet cannula.
4. The inlet cannula of claim 1, wherein the ingrowth zone includes a texturing.
5. The inlet cannula of claim 4, wherein the texturing is formed by a sintering process, a 3D printing process, a 3D printing process for imprinting a titanium texturing.
6. The inlet cannula of claim 4, wherein the texturing has a mean roughness depth of Rz>16 μm.
7. The inlet cannula of claim 4, wherein the texturing in only a portion of the ingrowth zone.
8. The inlet cannula of claim 4, wherein the texturing is formed by a bombardment with small spheres and/or by an adhesive bonding of a continuous fabric.
9. The inlet cannula of claim 1, wherein the inlet zone is polished, the polished inlet zone having a mean roughness depth of Rz<1.5 μm.
10. The inlet cannula of claim 1, wherein the ingrowth zone is concavely or convexly curved with a radius of curvature of 2 to 20 mm.
11. The inlet cannula of claim 1, wherein the inlet zone is convexly curved with a radius of curvature of 5, 10 or 15 mm.
12. The inlet cannula of claim 1, wherein the first tangent to the inlet zone and a second tangent to the ingrowth zone at the flow separation edge intersect at an angle between 40° and 150°.
13. The inlet cannula of claim 12, wherein the first tangent to the inlet zone and the second tangent to the ingrowth zone at the flow separation edge intersect at an angle of 90°.
14. The inlet cannula of claim 1, wherein a jump in wall shear stress between the fluid and the surface of the inlet cannula of at least 100% results at the transition from the ingrowth zone to the inlet zone.

15. The inlet cannula of claim 14, wherein the inlet cannula includes a pump interface for connecting the inlet cannula to a fluid pump, and a third tangent, which is perpendicular to the flow separation edge at the inlet zone in a region of the inlet zone adjacent to the pump interface, has an angle between 0° and 30° with respect to the longitudinal axis of the inlet cannula.

16. The inlet cannula of claim 1, wherein the inlet cannula has an inlet opening in a region of the inlet zone adjacent to the flow separation edge, and a lattice element, which partially closes the inlet opening, is arranged in the inlet opening.

17. A fluid pump system, comprising the inlet cannula of claim 1 and a fluid pump, a pump interface of the inlet cannula connected to a pump inlet of the fluid pump.

* * * * *